(12) United States Patent
Cullinane et al.

(10) Patent No.: US 12,115,312 B2
(45) Date of Patent: Oct. 15, 2024

(54) SECUREMENT DEVICE FOR A PROTRUDING ORAL OR NASAL DEVICE

(71) Applicant: LIVERPOOL UNIVERSITY HOSPITALS NHS FOUNDATION TRUST, Liverpool (GB)

(72) Inventors: Matthew John Cullinane, Bebington (GB); Robert Brothwood, Liverpool (GB)

(73) Assignee: LIVERPOOL UNIVERSITY HOSPITALS NHS FOUNDATION TRUST, Liverpool (GB)

( * ) Notice: Subject to any disclaimer, the term of this patent is extended or adjusted under 35 U.S.C. 154(b) by 737 days.

(21) Appl. No.: 17/296,273

(22) PCT Filed: Nov. 26, 2019

(86) PCT No.: PCT/GB2019/053336
§ 371 (c)(1),
(2) Date: May 24, 2021

(87) PCT Pub. No.: WO2020/109775
PCT Pub. Date: Jun. 4, 2020

(65) Prior Publication Data
US 2022/0339384 A1 Oct. 27, 2022

(30) Foreign Application Priority Data
Nov. 26, 2018 (GB) ...................... 1819185

(51) Int. Cl.
*A61M 16/04* (2006.01)
*A61M 16/06* (2006.01)
*A61M 25/02* (2006.01)

(52) U.S. Cl.
CPC .... *A61M 16/0497* (2013.01); *A61M 16/0666* (2013.01); *A61M 16/0688* (2014.02);
(Continued)

(58) Field of Classification Search
CPC ............ A61M 25/02; A61M 2025/026; A61M 2025/0253; A61M 16/0488;
(Continued)

(56) References Cited

U.S. PATENT DOCUMENTS

| 5,300,037 A | 4/1994 | Delk et al. |
| 5,308,339 A | 5/1994 | Kalt et al. |

(Continued)

FOREIGN PATENT DOCUMENTS

| CN | 203029790 U | 7/2013 |
| CN | 203139349 U | 8/2013 |

(Continued)

OTHER PUBLICATIONS

State Intellectual Property Office of People's Republic of China, Second Office Action CN No. 201980077651.1, Jun. 30, 2023, China.

(Continued)

*Primary Examiner* — Margaret M Luarca
(74) *Attorney, Agent, or Firm* — Taft Stettinius & Hollister LLP; Stephen F. Rost

(57) ABSTRACT

A securement device for a protruding oral or nasal device includes a continuous strip extending along a longitudinal axis between a first end and a second end. The continuous strip has a first anchor portion at the first end, a second anchor portion at the second end, a first bridge portion, a second bridge portion, and an adhesive for affixing the strip to a patient. The first bridge portion is disposed between the first anchor portion and the second bridge portion, the second bridge portion is disposed between the first bridge portion and the second anchor portion, the second bridge portion extends at an angle relative to the longitudinal axis. The first anchor portion and the second anchor portion are offset from one another relative to the longitudinal axis.

26 Claims, 5 Drawing Sheets

(52) U.S. Cl.
CPC .............. *A61M 2025/022* (2013.01); *A61M 2025/0226* (2013.01); *A61M 2025/0266* (2013.01)

(58) Field of Classification Search
CPC ...... A61M 16/0683; A61M 2025/0206; A61M 16/0487
See application file for complete search history.

(56) References Cited

U.S. PATENT DOCUMENTS

| | | | |
|---|---|---|---|
| 5,546,938 A | | 8/1996 | McKenzie |
| 5,735,272 A | * | 4/1998 | Dillon ................. A61F 5/08 |
| | | | 128/207.18 |
| 5,743,885 A | | 4/1998 | Gordon |
| 5,797,394 A | | 8/1998 | Boyd |
| 8,794,240 B1 | * | 8/2014 | Marcoe ............ A61M 16/0447 |
| | | | 128/207.14 |
| 2005/0171482 A1 | * | 8/2005 | Russo .................. A61M 25/02 |
| | | | 128/DIG. 26 |
| 2010/0199997 A1 | | 8/2010 | McInnes et al. |
| 2018/0235845 A1 | * | 8/2018 | Oliveira ............. A61J 15/0003 |

FOREIGN PATENT DOCUMENTS

| | | |
|---|---|---|
| CN | 203507284 U | 4/2014 |
| CN | 203694318 U | 7/2014 |
| CN | 203694352 U | 7/2014 |
| CN | 203694353 U | 7/2014 |
| CN | 204766966 U | 11/2015 |
| CN | 105517622 A | 4/2016 |
| CN | 105879180 A | 8/2016 |
| CN | 106823104 A | 6/2017 |
| CN | 107921238 A | 4/2018 |
| CN | 208114906 U | 11/2018 |
| TW | M498596 U | 4/2015 |
| TW | M531845 U | 11/2016 |
| WO | 1998010823 A1 | 3/1998 |

OTHER PUBLICATIONS

State Intellectual Property Office of People's Republic of China; Notification of the First Office Action of corresponding Application No. 20198007765.1; Issued: Nov. 3, 2022; pp. 1-8.
Intellectual Property Office of India, Examination Report, Indian Application No. 202137027732, Dec. 2, 2022, 7 pages.
International Search Report, European Patent Office, PCT/GB2019/053336, 2 pages, Mar. 6, 2020.
U.K. Search Report, UKIPO, GB1819185.8, 3 pages, Apr. 10, 2019.

* cited by examiner

SECUREMENT DEVICE FOR A PROTRUDING ORAL OR NASAL DEVICE

This application is a U.S. national stage application under 35 U.S.C. § 371 of PCT International Application Serial No. PCT/GB2019/053336 which has an international filing date of Nov. 26, 2019, designates the United States of America, and claims the benefit of GB Application No. 1819185.8, which was filed on Nov. 26, 2018. The disclosures of each of these prior applications are hereby expressly incorporated by reference in their entirety.

The present invention relates to a securement device for a protruding oral or nasal device including but not limited to an endotracheal tube, and in particular, to a securement device that comprises a continuous strip with an adhesive for affixing the strip to a patient.

BACKGROUND

Endotracheal intubation is an important procedure in both anaesthetized and critically ill patients. Endotracheal tube displacement is one of the leading causes for airway relates complications. Securing the endotracheal tube, therefore, is critically important in preventing accidental extubation, which can be life threatening.

Rates of unintentional extubation are found to range from 1.6% to 21% between anaesthesia and intensive care. In a study of 426 adult intensive care unit (ICU) patients, 10.8% experienced at least one episode of unplanned extubation, and it was found that a lack of a strong tube fixation was one of the major predisposing factors to unplanned extubation in ventilated adult patients.

There is a variety of commercially available products that seek to provide secure endotracheal tube fixation. These include the Thomas™ Endotracheal Tube holder which consists of a rigid plastic holder connected to an elasticated strap, and the Portex® RSP Tracheal Tube holder which consists of a slide-on locking device connected to an adhesive backed base. Products such as these are configured to connect to a tube of a particular size. Additionally, products with elasticated straps may lead to pressure sores on the patient. Fundamentally, however, complex products, such as those comprising multiple materials and/or plastics moulded parts have a high (relative) cost associated with them such that widespread adoption of the product across a medical facility (such as a hospital) can be prohibitively expensive.

An alternative to these products is to simply use medical tape to affix an endotracheal tube to a patient and this is often the most commonly practiced method. Whilst less costly than a dedicated fixation device, the use of medical tape is not without its disadvantages. In particular, once the packaging of a roll of medical tape is opened, the roll of tape is never cleaned or sterilized. While a single strip of tape may be single use, the roll itself is often the only piece of surgical equipment that is re-used and not sterilized. As such, the re-use of rolls of tape between patients presents a potential risk of introducing infection to the airway (or skin) of intubated patients.

Furthermore, given that medical tape is intended for a broad range of applications, it is not necessarily suited for application on the delicate skin of the face. Indeed, removal of medical tape from a patient's face can remove superficial layers of skin which can cause tears. In addition to causing patient discomfort, skin abrasions can also be a common entry point for bacteria including methicillin-resistant *Staphylococcus aureus* (MRSA).

US patent application publication US-A-2010/0199997 (McInnes et al.) describes a tracheal tube support apparatus that includes a pair of oppositely disposed adhesively mountable flanges for releasably mounting to the face of the patient. A pair of adhesive-backed wings is provided for releasable mounting to a portion of the tracheal tube once intubated.

An endotracheal tube is not the only device for which secure tube fixation is important. Secure fixation is also required for protruding oral or nasal devices such as supraglottic airways, oral monitoring devices such and nasogastric tubes. It is an object of certain embodiments of the present invention to provide a securement device for a protruding oral or nasal device that overcomes at least some advantages associated with the prior art. It is an object of certain embodiments of the present invention to provide an alternative securement device for a protruding oral or nasal device relative to the prior art.

BRIEF SUMMARY OF THE DISCLOSURE

In accordance with an aspect of the present invention there is provided a securement device for a protruding oral or nasal device, comprising a continuous strip extending along a longitudinal axis between a first end and a second end, the continuous strip having:
 a first anchor portion at the first end;
 a second anchor portion at the second end;
 a first bridge portion;
 a second bridge portion; and
 an adhesive for affixing the strip to a patient;
 wherein the first bridge portion is disposed between the first anchor portion and the second bridge portion, the second bridge portion is disposed between the first bridge portion and the second anchor portion, and the second bridge portion extends at an angle relative to the longitudinal axis.

In certain embodiments, the first anchor portion and the second anchor portion are offset from one another relative to the longitudinal axis.

The first bridge portion may be substantially aligned with the longitudinal axis.

The securement device may comprise a third bridge portion disposed between the second bridge portion and the second anchor portion, wherein the third bridge portion may be substantially aligned with the longitudinal axis.

Either or both of the first anchor portion and second anchor portion may include a plurality of limbs. The plurality of limbs may comprise a pair of limbs extending from one another, where the pair of limbs may form a V-shape. The pair of limbs may form an intersection angle of between 70° and 110°.

The strip may have a length along the longitudinal axis between 15 cm and 45 cm, and optionally about 30 cm.

The first bridge portion may extend along a length between 1 cm and 4 cm, and optionally about 2 cm.

The second bridge portion may extend along a length between 1 cm and 4 cm, and optionally about 2 cm.

The second bridge portion may extend at an angle of between 10° and 80°, and optionally about 45° relative to the longitudinal axis.

The adhesive is provided on a back side of the strip. The adhesive may be provided in selected regions of the back side of the strip. Alternatively, the adhesive may be provided substantially over the entire back side of the strip. The adhesive may comprise multiple adhesives or an adhesive having varying strengths across the strip.

In accordance with another aspect of the present invention, there is provided a kit comprising a packaging containing a securement device as defined above. The securement device may be in a sterile state in the packaging prior to opening of the packaging.

In accordance with another aspect of the present invention, there is provided an assembly comprising an oral or nasal device and a securement device as defined above, wherein the securement device is wound around the oral or nasal device such that the first anchor portion and the second anchor portion extend from opposite sides of the oral or nasal device.

In certain embodiments, the second bridge portion of the securement device may be wound around the oral or nasal device.

In accordance with another aspect of the present invention, there is provided a method of attaching a securement device to a protruding oral or nasal device and a patient comprising:

providing an oral or nasal device protruding from a patient;

providing a securement device as defined above;

winding the securement device around the oral or nasal device protruding from a patient and adhering the first anchor portion and the second anchor portion to the patient on opposite sides of the oral or nasal device.

In certain embodiments, winding the securement device around the tube may comprise winding the second bridge portion around the oral or nasal device.

In certain embodiments, the securement device may be wound around the oral or nasal device and the first anchor portion may be adhered to the patient so that the first bridge portion leads away from the first anchor portion towards the lips of the patient.

In certain embodiments, when either or both of the first anchor portion and second anchor portion include a plurality of limbs, a first limb of the plurality of limbs may be adhered in the region of the cheek bone of the patient and a second limb of the plurality of limbs may be adhered in the region of the jaw bone of the patient.

BRIEF DESCRIPTION OF THE DRAWINGS

Embodiments of the invention are further described hereinafter with reference to the accompanying drawings, in which.

DETAILED DESCRIPTION

Figure 1:
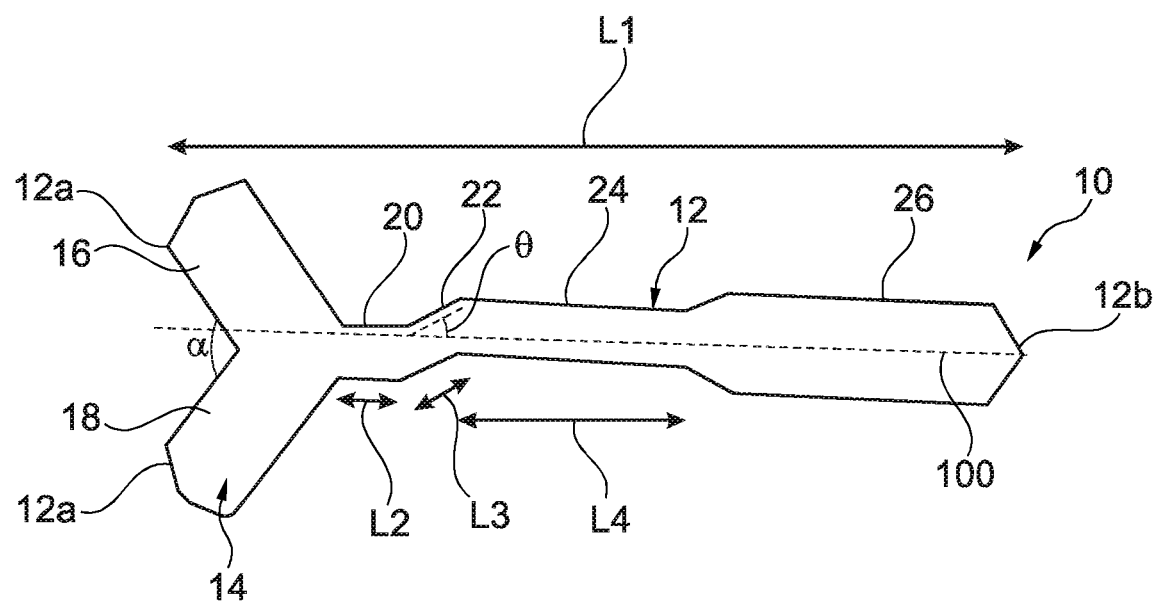
FIG. 1 shows a securement device in accordance with an embodiment of the present invention.

A securement device 10 according to an embodiment of the present invention is shown in FIG. 1. The securement device 10 is suitable for the securement of a protruding oral or nasal device (not shown in FIG. 1). The securement device 10 comprises a strip 12 that extends along a longitudinal axis 100 between a first end 12a and a second end 12b. An adhesive (not visible in the Figures) is provided on a back side of the strip 12 for affixing the strip 12 to a patient. The strip 12 includes a first anchor portion 14 at the first end 12a and a second anchor portion 26 at the second end 12b.

Between the first end 12a and second end 12b, the strip 12 includes a first bridge portion 20, a second bridge portion 22 and a third bridge portion 24. More specifically, the first bridge portion 20 is disposed between the first anchor portion 14 and the second bridge portion 22, the second bridge portion 22 is disposed between the first bridge portion 20 and the third bridge portion 24, and the third bridge portion 24 is disposed between the second bridge portion 22 and the second anchor portion 26. In the embodiment shown in FIG. 1, each of the first bridge portion 20 and the third bridge portion 24 is substantially parallel to the longitudinal axis 100 (and one another). The second bridge portion 22 extends at an inclined angle θ relative to the longitudinal axis 100 and each of the first bridge portion 20 and the third bridge portion 24. The first anchor portion 14 and the second anchor portion 26 are offset from one another relative to the longitudinal axis 100. That is, the first anchor portion 14 extends from the longitudinal axis 100 by an amount that differs from the amount that the second anchor portion 26 extends from the longitudinal axis 100 in the same direction.

The strip 12 has a length L1 (taken along its longitudinal axis 100 between the first end 12a and second end 12b). The first bridge portion 20 has a length L2, the second bridge portion 22 extends along a length L3, while the third bridge portion 24 extends along a length L4. In certain non-limiting embodiments, L1 is between 15 cm and 45 cm and is optionally around 30 cm, and/or L2 is between 1 cm and 4 cm and is optionally around 2 cm, and/or L3 is between 1 cm and 4 cm and is optionally around 2 cm, and/or L4 is between 4 cm and 12 cm and is optionally around 8 cm. In certain non-limiting embodiments, the inclination angle θ of the second bridge portion 22 relative to the longitudinal axis 100 is between 10° and 80° and is optionally around 45°. Notwithstanding the above mentioned example lengths and angles, embodiments of the present invention may encompass other lengths and angles.

In the illustrated embodiment, the first anchor portion 14 comprises a first limb 16 and a second limb 18 that extend from one another in a V-shape and form an intersection angle α. In certain embodiments, the intersection angle α may be between 70° and 110° and may optionally be around 90°. The first limb 16 is configured to attach to the face of a patient in the region of the patient's cheek bone whilst the second limb 18 is configured to attach to the face of the patient face in the region of the jaw bone. The relative lengths of the first limb 16 and second limb 18 and the magnitude of the intersection angle α may therefore be configured so that the first anchor portion 14 may affix to the cheek and jaw bone of a certain patient or group of patients. That is, in certain embodiments the first limb 16, second limb 18 and intersection angle α may be configured so that the first anchor portion 14 may affix to the cheek and jaw bone of an adult patient, whereas in other embodiments, the first limb 16, second limb 18 and intersection angle α may be configured so that the first anchor portion 14 may affix to the cheek and jaw bone of an infant patient.

In the illustrated embodiment, the second anchor portion 26 comprises a single limb that extends substantially parallel to the longitudinal axis 100 away from the third bridge portion 24.

In other embodiments, either or both of the first anchor portion 14 and the second anchor portion 26 may include any number of limbs that extend from one another. The limbs may form a V-shape or other configuration, and the limbs may form any suitable intersection angle.

Figure 2:
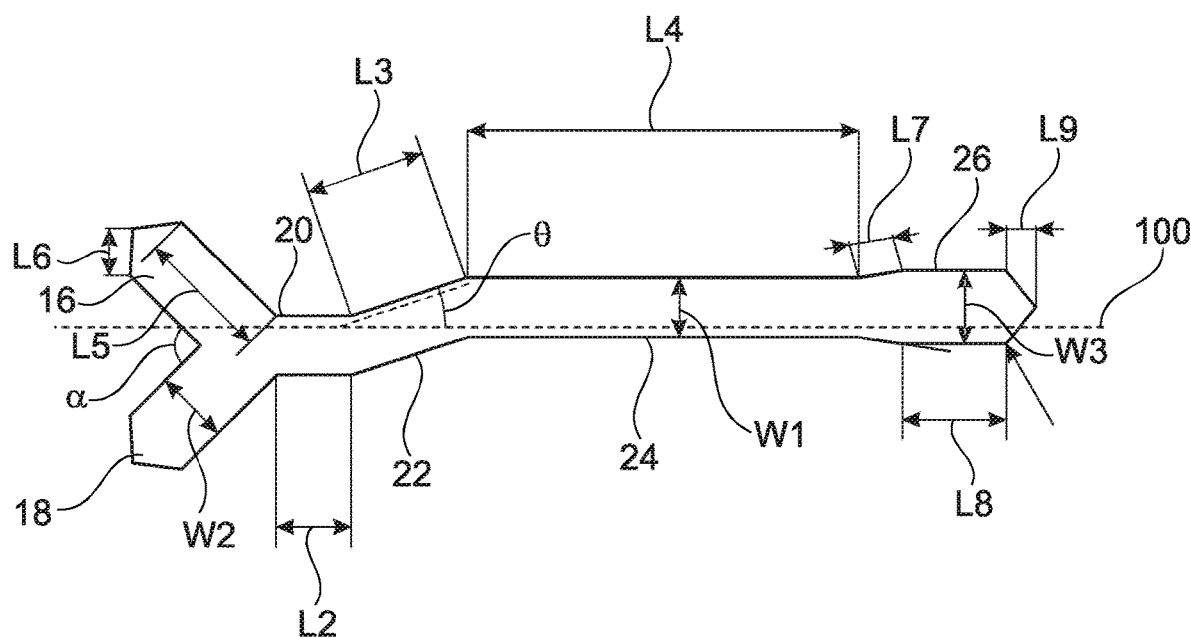
FIG. 2 shows an example of the relative dimensions of a securement device in accordance with another embodiment of the present invention.

A non-limiting example of the relative lengths of the bridge portions and anchor portions of the securement device 10 is shown in FIG. 2. In the example, the width W1 of the third bridge portion 24 is shown as equal to 1.00 and all other dimensions in the example are provided relative to W1. In this non-limiting example, the first bridge portion 20 has a length L2 equal to 1.25, the second bridge portion has a length L3 equal to 2.00 and the third bridge portion has a length L4 equal to 6.50. The inclination angle θ of the second bridge portion 22 relative to the longitudinal axis 100 is 18.97°. In this example, the first anchor portion 14 comprises a first limb 16 and a second limb 18. The first limb 16 and the second limb 18 have a width W2 equal to 1.25 and a length L5 equal to 2.25. The first and second limbs are each inclined at an angle of 135.20° relative to the longitudinal axis 100, as such, the intersection angle α is 89.60°. The first limb and second limb each have a tapered portion at the first end 12a of the strip 12, the tapered portions have a length L6 equal to 0.80. In this example, the second anchor portion comprises: a first portion with a length L7 equal to 0.75 which inclined at an angle of 9.59° relative to the longitudinal axis 100; a second portion substantially parallel to the longitudinal axis 100 with a length L8 equal to 1.75 and a width W3 equal to 1.25; and a third tapered portion at the second end 12b of the strip 12 that has a length L9 equal to 0.50 in the direction parallel to the longitudinal axis 100.

Figure 3:
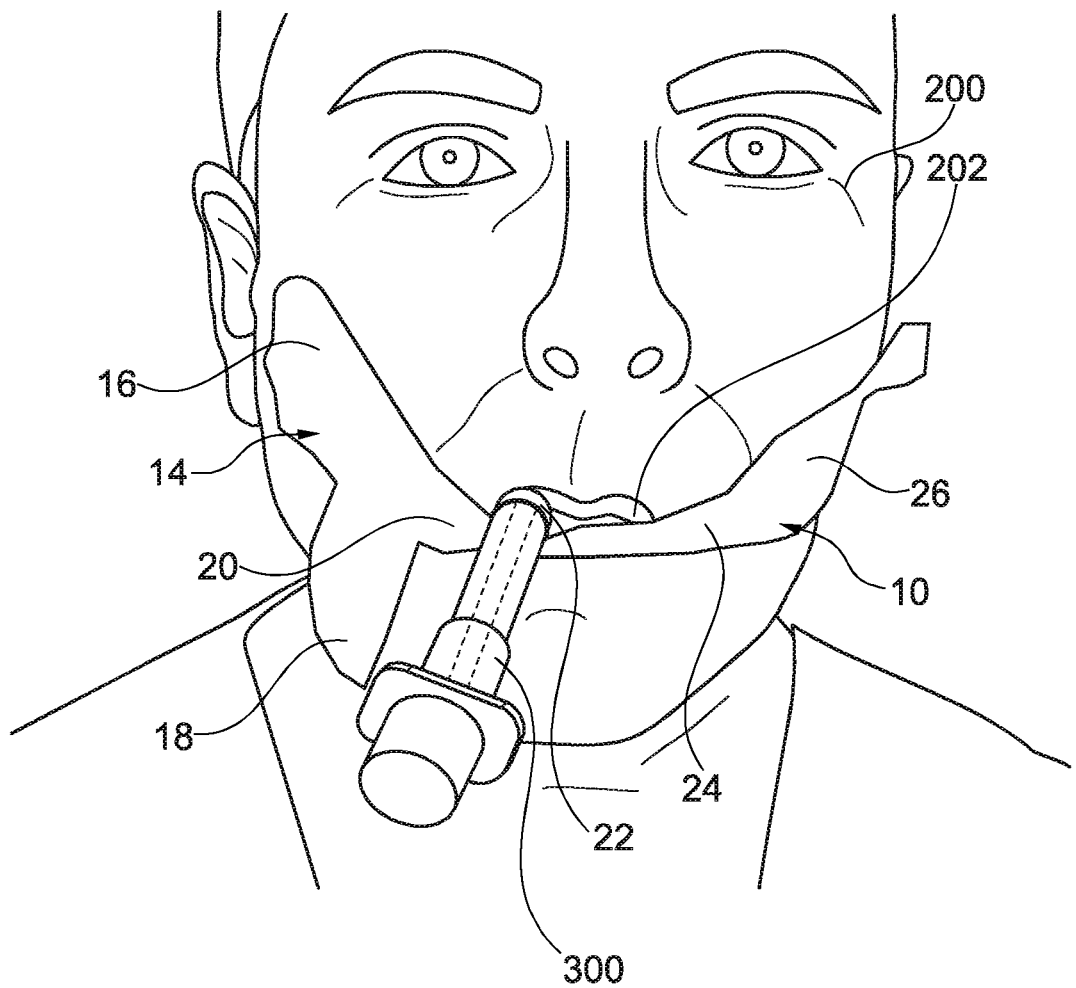
FIG. 3 shows a front view of a patient with an endotracheal tube secured thereto by a securement device according to an embodiment of the present invention.
Figure 4:
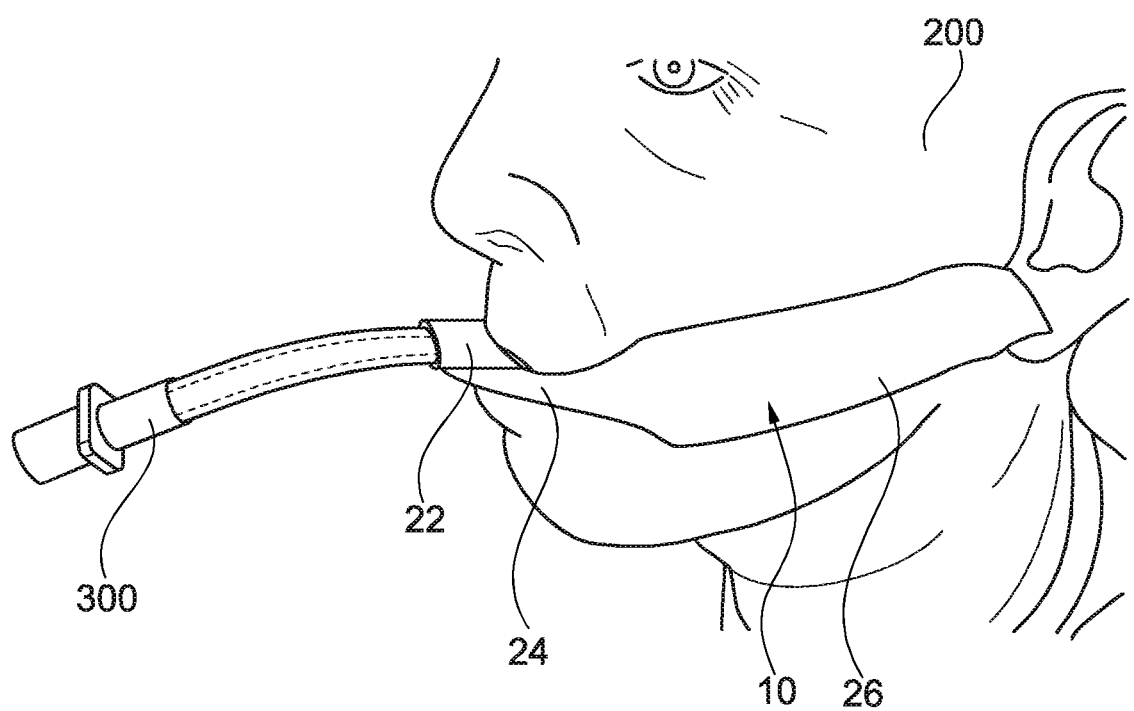
FIG. 4 shows a side view of the patient of FIG. 3.

In use, the strip 12 is wound around a protruding oral or nasal device and is affixed to the patient's face by the adhesive on the back side of the strip 12. The protruding oral or nasal devices may include but are not limited to: endotracheal tubes such as standard endotracheal tubes, south facing endotracheal tubes, north facing endotracheal tubes, armoured or flexible endotracheal tubes, microlaryngoscopy tubes, double lumen endotracheal tubes, nasal endotracheal tubes and low pressure endotracheal tubes; supraglottic airways including standard laryngeal mask and flexible or armoured laryngeal masks; oral monitoring devices such as temperature probes and oesophageal dopplers; and nasogastric tubes. Indeed, the protruding oral or nasal device may include any device that protrudes form a patient's oral or nasal cavity. FIGS. 3 and 4 show examples of an endotracheal tube 300 secured to a patient 200 using a securement device 10 in accordance with an embodiment of the present invention.

As shown in FIGS. 3 and 4, the strip 12 is wound around the endotracheal tube 300 and is adhered to the face of the patient 200. In particular, the first limb 16 is adhered to the face of the patient 200 in the region of the cheek bone and the second limb 18 is adhered to the patient 200 in the region of the jaw bone. The first bridge portion 20 leads away from the first anchor portion 14 towards the lips 202 of the patient 200. The second bridge portion 22 is wound around the endotracheal tube 300. Advantageously, due to the inclination angle θ of the second bridge portion 22 relative to the longitudinal axis 100 of the strip 12 (and/or the first bridge portion 20), the second bridge portion 22 may wind around the endotracheal tube 300 such that the adhesive back side of the strip 12 is substantially affixed to the endotracheal tube 300 rather than the strip 12 itself. That is, the configuration of the second bridge portion 22 relative to the first bridge portion 20 may facilitate a secure winding of the strip 12 around the endotracheal tube 300 whilst avoiding winding of the strip 12 on itself. In particular, this configuration may also maximise the contact of the adhesive back side of the strip 12 to the endotracheal tube 300 whilst avoiding kinks being formed in the strip 12 as it is wound around the endotracheal tube 300.

Additionally, the configuration of the second bridge portion 22 relative to the first bridge portion 20 permits the strip 12 to be wound below the endotracheal tube 300 such that the strip 12 may be affixed to the face of the patient 200 below the lips 202 of the patient. This is advantageous as it may permit the lips 202 of the patient 200 to remain visible during surgical procedures thereby allowing any colour change of the lips 202, which may be an indication of blood oxygen levels, to be monitored. A further advantage of a winding around the endotracheal tube 300 that is below the lips 202 of the patient 200 is that the potential infection risk to the patient 200 is reduced since the securement device 10 is not in close proximity to the nose of the patient 200 (which is a major entry point for infection).

The third bridge portion 24 extends substantially parallel to the longitudinal axis 100 beneath the lips 202. By extending substantially parallel to the longitudinal axis 100, the third bridge portion 24 may extend so that (at least) the entire top lip 202 remains visible. In other embodiments, the third bridge portion 24 may not be substantially parallel to the longitudinal axis 100 such that at least some of the lips 202 may be obscured by the third bridge portion 24.

In certain embodiments, the third bridge portion 24 may be omitted entirely. That is, two bridge portions may be present between the first anchor portion 14 and the second anchor portion 26, where one of the bridge portions may be inclined relative to the longitudinal axis 100 of the strip 12. In such embodiments, one of the two bridge portions may extend between the endotracheal tube 300 (when attached thereto) and the second anchor portion 26. In other embodiments, additional bridge portions may be provided between the first anchor portion 14 and the second anchor portion 26. The additional bridge portions may be parallel to or inclined relative to the longitudinal axis 100.

Due to the asymmetry of the securement device 10, the endotracheal tube 300 may be secured at one side of the patient's mouth. In other embodiments, the relative lengths of the bridge portions 20, 22, 24 may be such that the endotracheal tube 300 is secured around the centre of the patient's mouth. Although the use of the securement device 10 is described in relation to use with endotracheal tubes, the securement device may be similarly used with other oral and nasal devices and provide similar advantages.

Figure 5:
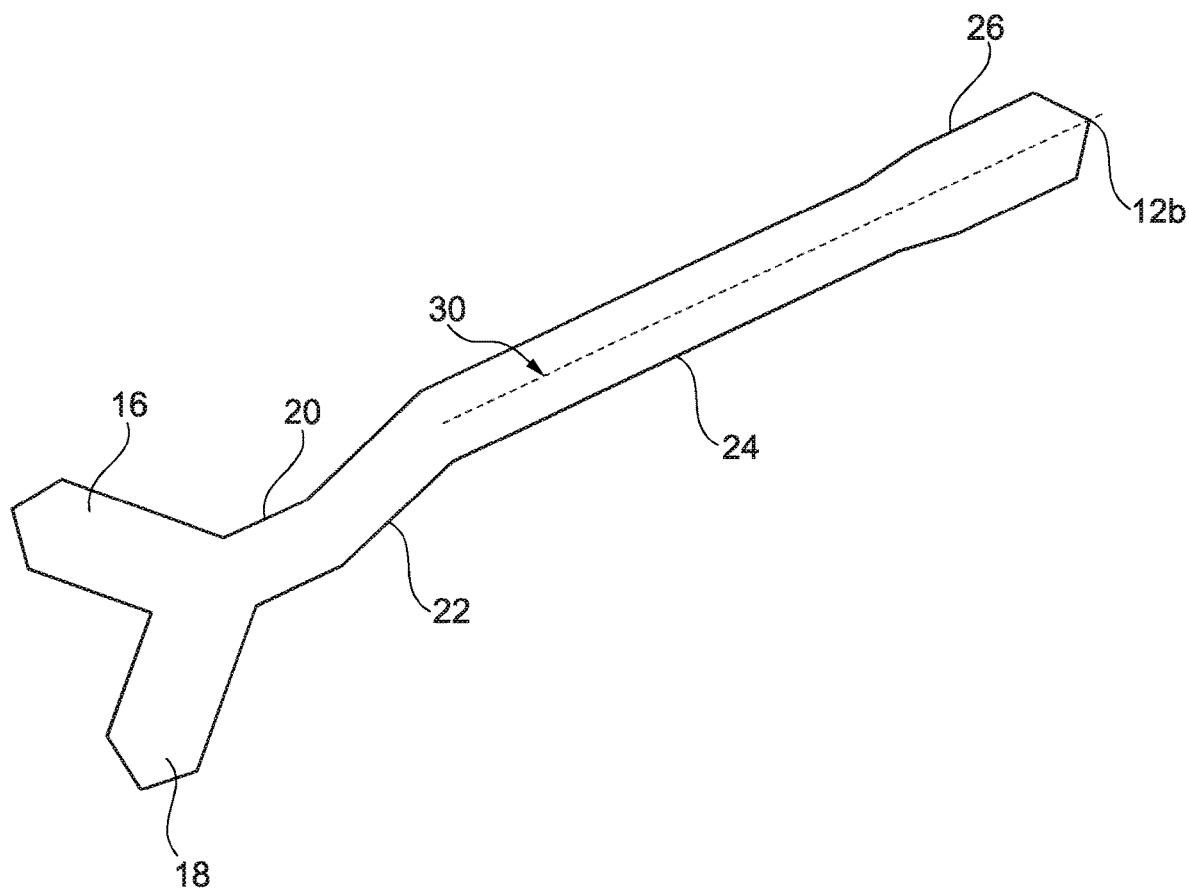
FIG. 5 shows a securement device in accordance with another embodiment of the present invention.

In certain embodiments, the securement device 10 may be perforated along the longitudinal axis 100. The perforation of the securement device 10 may extend along the longitudinal axis from the second end 12b. The perforation may extend along the length of the second anchor portion 26. The perforation may also extend at least partially into the third bridge portion 24. In the non-limiting embodiment shown in FIG. 5, the perforation of the securement device 10 extends along the second anchor portion 26 and the third bridge portion 24, and is illustrated by a dashed line 30 which lies on the longitudinal axis (not shown). The perforation of the securement device 10 enables the second anchor portion 26 to be separated into two strips. The separation of the second anchor portion 26 may advantageously improve the fixation of the securement device 10 to a patient for certain positions of the oral or nasal device.

The adhesive may be provided on the back side of the strip 12 and may be initially covered with a removable cover material. When the securement device 10 is to be used, the cover material may be removed to expose the adhesive and the adhesive may subsequently be used to affix the strip 12 to the oral or nasal device, and the strip 12 to the face of the patient 200. The adhesive may be provided over the entire surface of the back side of the strip 12 or the adhesive may be provided on one or more selected regions of the back side of the strip 12. The adhesive is preferably one that provides an adequate securement of the strip 12 to the patient and/or the oral or nasal device but is not so strong that the skin of the patient is significantly damaged when the strip 12 is removed therefrom. Ideally, the adhesive strikes a balance between providing security of fitting whilst minimizing skin damage. In certain embodiments, multiple adhesives or an adhesive having varying strengths may be provided on the strip 12. For example, a different adhesive may be provided for securing the strip 12 to the oral or nasal device relative to the adhesive provided for affixing the strip 12 to the face of the patient 200.

The securement device 10 may comprise any suitable material. In selecting a suitable material for the securement device 10 consideration may be given to: the integrity of the material (i.e. signs of peeling, wrinkling or moisture absorption of the material during use); the ease of removal from a patient; and the kindness of the material to the patient's skin (i.e. whether the tape causes redness, soreness, irritation, abrasions or tearing of the skin). An example of a suitable material for the securement device 10 is a medical tape. A preferred example of a suitable medical tape for the securement device 10 is 3M™ Microfoam Surgical Tape 1528. It has been found that 3M™ Microfoam Surgical Tape 1528 performs better than other examples of medical tapes with regard to material integrity, ease of removal and kindness to skin. The tape comprises a poly(vinyl chloride) foam layer with an acrylate adhesive. An alternative example of a suitable medical tape is the 3M™ Medical White Rayon Nonwoven Tape 1530 which comprises a non-woven rayon tape with a pressure sensitive, hypoallergenic acrylate adhesive. Another example of a suitable medical tape is the 3M™ Single Coated Polyolefin Medical Tape 1527 which comprises a perforated polyolefin tape coated with a pressure sensitive, hypoallergenic acrylate adhesive.

The securement device 10 may be sterile and be provided in a sterile package that may be opened when required to provide the sterile securement device 10. In preferable embodiments, the securement device 10 may be intended for a single use and may be disposed after a single use.

Embodiments of the present invention may improve patient safety by reducing rates of infection and/or accidental extubation. Additionally or alternatively, patient experience may be improved by reducing the likelihood and severity of skin tears on the face (e.g. the lips). As such, the length of stay in hospital may be reduced for patients and costs associated with hospital acquired infections (HAIs) may be reduced.

Embodiments of the present invention may be less costly in comparison to prior art securement devices which include multiple materials and/or moulded parts. Additionally, embodiments of the present invention may provide improved versatility relative to prior art devices, since the present invention is not necessarily limited to use with oral or nasal devices of any particular diameter. Securement devices 10 according to embodiments of the present invention may be more secure and less damaging to the skin relative to standard medical tape. Furthermore, securement devices 10 according to embodiments of the present invention may reduce infection risk relative to a roll of tape which may be used on multiple patients. Indeed, the use of a securement device 10 in accordance with embodiments of the present invention may help to introduce new best practice in hospitals given its suitability to single usage.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A securement device for a protruding oral or nasal device, comprising a continuous strip extending along a longitudinal axis between a first end and a second end, the continuous strip comprising:
 a first anchor portion at the first end;
 a second anchor portion at the second end;
 a first bridge portion;
 a second bridge portion; and
 an adhesive for affixing the strip to a patient;
 wherein the first bridge portion is disposed between the first anchor portion and the second bridge portion, the second bridge portion is disposed between the first bridge portion and the second anchor portion, the second bridge portion is configured to be wound around the protruding oral or nasal device by extending at an angle relative to the longitudinal axis, and the first anchor portion and the second anchor portion are offset from one another relative to the longitudinal axis.

2. The securement device of claim 1, wherein the first bridge portion is substantially aligned with the longitudinal axis.

3. The securement device of claim 1, comprising a third bridge portion disposed between the second bridge portion and the second anchor portion.

4. The securement device of claim 3, wherein the third bridge portion is substantially aligned with the longitudinal axis.

5. The securement device of claim 1, wherein either or both of the first anchor portion and second anchor portion includes a plurality of limbs.

6. The securement device of claim 5, wherein the plurality of limbs comprises a pair of limbs extending from one another.

7. The securement device of claim 6, wherein the pair of limbs forms a V-shape.

8. The securement device of claim 7, wherein the pair of limbs forms an intersection angle of between 70° and 110°.

9. The securement device of claim 1, wherein the strip has a length along the longitudinal axis between 15 cm and 45 cm, and optionally about 30 cm.

10. The securement device of claim 1, wherein the first bridge portion extends along a length between 1 cm and 4 cm, and optionally about 2 cm.

11. The securement device of claim 1, wherein the second bridge portion extends along a length between 1 cm and 4 cm, and optionally about 2 cm.

12. The securement device of claim 1, wherein the second bridge portion extends at an angle of between 10° and 80°, and optionally about 45° relative to the longitudinal axis.

13. The securement device of claim 1, wherein the adhesive is provided on a back side of the strip.

14. The securement device of claim 13, wherein the adhesive is provided in selected regions of the back side of the strip.

15. The securement device of claim 13, wherein the adhesive is provided substantially over the entire back side of the strip.

16. The securement device of claim 1, wherein the adhesive comprises multiple adhesives or an adhesive having varying strengths.

17. The securement device of claim 1, comprising a perforation along the second anchor portion.

18. The securement device of claim 17, wherein the perforation extends from the second end along the longitudinal axis.

19. The securement device of claim 17, wherein the perforation extends into the bridge portion adjacent to the second anchor portion.

20. A kit comprising a packaging containing a securement device according to claim 1.

21. The kit of claim 20, wherein the securement device is in a sterile state in the packaging prior to opening of the packaging.

22. An assembly comprising:
an oral or nasal device;
a securement device according to claim 1;
wherein the securement device is configured to be wound around the oral or nasal device such that the first anchor portion and the second anchor portion extend from opposite sides of the oral or nasal device.

23. A method of attaching a securement device to a protruding oral or nasal device and a patient comprising:
providing an oral or nasal device protruding from a patient;
providing a securement device according to claim 1;
winding the securement device around the oral or nasal device protruding from a patient and
adhering the first anchor portion and the second anchor portion to the patient on opposite sides of the oral or nasal device.

24. The method of claim 23, wherein winding the securement device around the oral or nasal device comprises winding the second bridge portion around the oral or nasal device.

25. The method of claim 23, wherein the securement device is wound around the oral or nasal device and the first anchor portion is adhered to the patient so that the first bridge portion leads away from the first anchor portion towards the lips of the patient.

26. The method of claim 23,
wherein either or both of the first anchor portion and second anchor portion includes a plurality of limbs;
wherein a first limb of the plurality of limbs is adhered in the region of a cheek bone of a patient and a second limb of the plurality of limbs is adhered in a region of a jaw bone of the patient.

* * * * *